United States Patent
Cohen et al.

(10) Patent No.: US 9,591,984 B2
(45) Date of Patent: Mar. 14, 2017

(54) ALTERNANS AND PHARMACOLOGICAL AGENTS

(75) Inventors: Richard J. Cohen, Chestnut Hill, MA (US); Ali Haghighi-Mood, Andover, MA (US)

(73) Assignee: Spacelabs Healthcare, Inc., Snoqualmie, WA (US)

( * ) Notice: Subject to any disclaimer, the term of this patent is extended or adjusted under 35 U.S.C. 154(b) by 1628 days.

(21) Appl. No.: 12/630,718

(22) Filed: Dec. 3, 2009

(65) Prior Publication Data

US 2010/0145204 A1 Jun. 10, 2010

Related U.S. Application Data

(60) Provisional application No. 61/120,161, filed on Dec. 5, 2008.

(51) Int. Cl.
 *A61B 5/0452* (2006.01)
 *A61B 5/00* (2006.01)

(52) U.S. Cl.
 CPC .......... *A61B 5/0452* (2013.01); *A61B 5/7203* (2013.01)

(58) Field of Classification Search
 USPC ....................................................... 600/517
 See application file for complete search history.

(56) References Cited

U.S. PATENT DOCUMENTS

| | | | |
|---|---|---|---|
| 2001/0029338 A1 | 10/2001 | Krishnamachari | |
| 2002/0052539 A1* | 5/2002 | Haller et al. | 600/300 |
| 2005/0010124 A1 | 1/2005 | Couderc et al. | |
| 2005/0107836 A1 | 5/2005 | Noren | |
| 2005/0222512 A1 | 10/2005 | Hadley et al. | |
| 2005/0222513 A1 | 10/2005 | Hadley et al. | |
| 2005/0234355 A1 | 10/2005 | Rowlandson | |
| 2006/0116596 A1* | 6/2006 | Zhou et al. | 600/516 |
| 2006/0206033 A1 | 9/2006 | Guerrero et al. | |
| 2007/0010753 A1 | 1/2007 | MacAdam | |
| 2007/0191890 A1* | 8/2007 | Armoundas et al. | 607/9 |
| 2007/0244402 A1 | 10/2007 | Brockway et al. | |
| 2007/0265538 A1* | 11/2007 | Badilini | 600/509 |

OTHER PUBLICATIONS

PCT International Search Report issued in PCT International Application No. PCT/US09/66759 mailed Mar. 23, 2010.
PCT International Search Report issued in PCT International Application No. PCT/US09/66769 mailed Mar. 23, 2010.
PCT International Search Report issued in PCT International Application No. PCT/US09/66765 mailed Apr. 22, 2010.

* cited by examiner

*Primary Examiner* — William Levicky
(74) *Attorney, Agent, or Firm* — Novel IP

(57) ABSTRACT

First cardiac signal data generated from measured heart beats of a subject is received. Characteristics of alternans occurring in the received first cardiac signal data are determined. Second cardiac signal data generated from measured heart beats of the subject after a change relating to an administration of a pharmacological agent is received. Characteristics of alternans occurring in the received second cardiac signal data are determined. The characteristics of alternans occurring in the received first cardiac signal data are compared with the characteristics of alternans occurring in the received second cardiac signal data.

27 Claims, 9 Drawing Sheets

A heart rate profile of first cardiac signal data stored by an AED

700

A heart rate profile of segmented first cardiac signal data generated from the first cardiac signal data

800

Sorted first cardiac signal data generated from the segmented first cardiac signal data

ALTERNANS AND PHARMACOLOGICAL AGENTS

CROSS-REFERENCE TO RELATED APPLICATIONS

This application claims priority to U.S. Provisional Application No. 61/120,161, which was filed on Dec. 5, 2008 and titled "ALTERNANS AND PHARMACOLOGICAL AGENTS," which is incorporated by reference in its entirety.

TECHNICAL FIELD

This disclosure is directed to the measurement of alternans and the use of pharmacological agents.

BACKGROUND

Pharmacological agents can exhibit unintended effects on a patient. These effects can range from mild to severe and can increase the risk of cardiac problems. In particular, a wide variety of pharmacological agents can increase a patient's risk of sudden cardiac death, cardiac arrest, and arrhythmias. Furthermore, a drug may put one patient at risk but not another patient. It is important to determine whether a drug increases a patient's risk of cardiac complications.

SUMMARY

In general, in some aspects, a method includes receiving first cardiac signal data generated from measured heart beats of a subject and determining characteristics of alternans occurring in the received first cardiac signal data. The method also includes receiving second cardiac signal data generated from measured heart beats of the subject after a change relating to an administration of a pharmacological agent and determining characteristics of alternans occurring in the received second cardiac signal data. The method additionally includes comparing the characteristics of alternans occurring in the received first cardiac signal data with the characteristics of alternans occurring in the received second cardiac signal data.

This and other implementations can optionally include one or more of the following features, which also may optionally be in any combination. For example, receiving first cardiac signal data can include accessing stored cardiac signal data from a non-volatile data storage. Receiving first cardiac signal data can include accessing cardiac signal data from volatile data storage which has not been stored in a non-volatile data storage. Receiving first cardiac signal data can include receiving data generated from measured heart beats of a subject occurring prior to administration of the pharmacological agent and receiving second cardiac signal data can include receiving data generated from measured heart beats of a subject occurring after administration of the pharmacological agent.

Also, determining characteristics of alternans occurring in the received first cardiac signal data can include determining whether alternans is present in the received first cardiac signal data, determining characteristics of alternans occurring in the received second cardiac signal data can include determining whether alternans is present in the received second cardiac signal data, and comparing the characteristics can include determining a difference between the presence of alternans in the received first cardiac signal data with the presence of alternans in the received second cardiac signal data. Determining characteristics of alternans occurring in the received first cardiac signal data can include determining a power or magnitude of alternans present in the received first cardiac signal data, determining characteristics of alternans occurring in the received second cardiac signal data can include determining a power or magnitude of alternans present in the received second cardiac signal data, and comparing the characteristics can include determining a difference between the power or magnitude of alternans in the received first cardiac signal data with the power or magnitude of alternans in the received second cardiac signal data. Determining characteristics of alternans occurring in the received first cardiac signal data can include determining an onset heart rate of alternans present in the received first cardiac signal data, determining characteristics of alternans occurring in the received second cardiac signal data can include determining an onset heart rate of alternans present in the received second cardiac signal data, and comparing the characteristics can include determining a difference between the onset heart rate of alternans in the received first cardiac signal data with the onset heart rate of alternans in the received second cardiac signal data.

Further, determining characteristics of alternans occurring in the received first cardiac signal data can include determining a maximum negative heart rate in the received first cardiac signal data, determining characteristics of alternans occurring in the received second cardiac signal data can include determining a maximum negative heart rate in the received second cardiac signal data, and comparing the characteristics can include determining a difference between the maximum negative heart rate in the received first cardiac signal data with the maximum negative heart rate in the received second cardiac signal data. Determining characteristics of alternans occurring in the received first cardiac signal data can include determining a presence or absence of alternans sustained for a period of time in the received first cardiac signal data, determining characteristics of alternans occurring in the received second cardiac signal data can include determining a presence or absence of alternans sustained for a period of time in the received second cardiac signal data, and comparing the characteristics can include determining the presence or absence of alternans sustained for a period of time in the received first cardiac signal data with the presence or absence of alternans sustained for a period of time in the received second cardiac signal data.

The method can include determining, based upon the comparison, a difference in the subject's risk for ventricular tachyarrhythmias prior to the change relating to the administration of the pharmacological agent from the subject's risk for ventricular tachyarrhythmias after the change relating to the administration of the pharmacological agent. The method can also include using the difference in the subject's risk for ventricular tachyarrhythmias to determine whether the pharmacological agent's use should be continued as treatment for an existing condition. The method can further include using the results of the comparison to assess the viability of the pharmacological agent for non-patient-specific use. The method can additionally include rendering results of the comparison. Determining characteristics of the alternans occurring in the received first cardiac signal data can include determining characteristics of T-wave alternans occurring in the received first cardiac signal data, determining characteristics of the alternans occurring in the received second cardiac signal data can include determining characteristics of T-Wave alternans occurring in the received second cardiac signal data, and comparing the characteristics of alternans occurring in the received first cardiac signal data with the characteristics of alternans occurring in the received second cardiac signal data can include comparing the characteristics of the T-wave alternans occurring in the received first cardiac signal data with the characteristics of the T-wave alternans occurring in the received second cardiac signal data.

In addition, determining characteristics of the alternans occurring in the received first cardiac signal data can include determining characteristics of ST segment alternans occurring in the received first cardiac signal data, determining characteristics of the alternans occurring in the received second cardiac signal data can include determining characteristics of ST segment alternans occurring in the received second cardiac signal data, and comparing the characteristics of alternans occurring in the received first cardiac signal data with the characteristics of alternans occurring in the received second cardiac signal data can include comparing the characteristics of the ST segment alternans occurring in the received first cardiac signal data with the characteristics of the ST segment alternans occurring in the received second cardiac signal data. Determining characteristics of the alternans occurring in the received first cardiac signal data can include determining characteristics of QRS complex alternans occurring in the received first cardiac signal data, determining characteristics of the alternans occurring in the received second cardiac signal data can include determining characteristics of QRS complex alternans occurring in the received second cardiac signal data, and comparing the characteristics of alternans occurring in the received first cardiac signal data with the characteristics of alternans occurring in the received second cardiac signal data can include comparing the characteristics of the QRS complex alternans occurring in the received first cardiac signal data with the characteristics of the QRS complex alternans occurring in the received second cardiac signal data.

Also, the method can additionally include determining QT prolongation or ST segment changes occurring in the received first cardiac signal data, determining QT prolongation or ST segment changes occurring in the received second cardiac signal data, and comparing the QT prolongation or ST segment changes occurring in the received first cardiac signal data with the QT prolongation or ST segment changes occurring in the received second cardiac signal data. The method can also include assessing, based on the comparing of the characteristics of alternans occurring in the received first cardiac signal data with the characteristics of alternans occurring in the received second cardiac signal data, a risk of sudden cardiac death, sudden cardiac arrest, arrhythmias, or sudden infant death, or the presence of cardiac ischemia. Receiving the first cardiac signal data generated from measured heart beats of the subject can include receiving, from an ambulatory electrocardiographic device, the first cardiac signal data generated from measured heart beats of the subject. Receiving the second cardiac signal data generated from measured heart beats of the subject after the change relating to the administration of the pharmacological agent can include receiving, from the ambulatory electrocardiographic device, the second cardiac signal data generated from measured heart beats of the subject after the change relating to the administration of the pharmacological agent.

In other implementations, some aspects include a system that includes sensors configured to measure electrical activity of heart beats, an amplifier configured to amplify the electrical activity, an analog to digital converter configured to convert the electrical activity to cardiac signal data, a user input control configured to enable a user to indicate a change relating to an administration of a pharmacological agent, and a processor. The processor is configured to generate first cardiac signal data when the user input control is not used to indicate the change relating to the administration of the pharmacological agent, and to generate second cardiac signal data when the user input control is used to indicate the change relating to the administration of the pharmacological agent. The second cardiac signal data is associated with an indication of the occurrence of the change relating to the administration of the pharmacological agent.

This and other implementations can optionally include one or more of the following features, which also may optionally be in any combination. For example, the device can be an ambulatory electrocardiography device. To generate the first cardiac signal data, the processor can be configured to generate first cardiac signal data segments each including cardiac signal data of sequential heart beats and to store the first cardiac signal data as multiple first cardiac signal data segments. To generate the second cardiac signal data, the processor can be configured to generate second cardiac signal data segments each including cardiac signal data of sequential heart beats, and the processor can be configured to store the second cardiac signal data as multiple second cardiac signal data segments. The processor can be configured to store each segment of the multiple second cardiac signal data segments with a data header indicating the change relating to the administration of the pharmacological agent and to store each segment of the multiple first cardiac signal data segments either without the data header indicating the change relating to the administration of the pharmacological agent or with a data header indicating an absence of the change relating to the administration of the pharmacological agent.

Also, the processor can be configured to generate the first and second cardiac signal data segments such that the sequential order of the heart beats as measured by the sensors is maintained within the cardiac signal data segments. The processor can be configured to generate the first and second cardiac signal data segments such that the cardiac signal data in each cardiac signal data segment partially overlaps the cardiac signal data of another cardiac signal data segment.

The system can also include a non-volatile storage unit configured to interface with multiple devices. The processor can be configured to store the first and second cardiac signal data on the non-volatile storage unit along with an indication of when the user input control is used to indication the change relating to the administration of the pharmacological agent. The non-volatile storage unit can be a flash drive.

Further, the processor can be configured to determine characteristics of alternans occurring in the first cardiac signal data, store the determined characteristics of alternans occurring in the first cardiac signal, determine characteristics of alternans occurring in the second cardiac signal data, and store the determined characteristics of alternans occurring in the second cardiac signal. The processor can be configured to compare the characteristics of alternans occurring in the first cardiac signal data with the characteristics of alternans occurring in the second cardiac signal data and store results of the comparison of the characteristics. To determine characteristics of alternans occurring in the first and second cardiac signal data, the processor can be configured to determine a presence of alternans in the first and second cardiac signal data.

Moreover, to determine characteristics of alternans occurring in the first cardiac signal data, the processor can be configured to determine an onset heart rate of or a maximum negative heart rate for the first cardiac signal data and to determine characteristics of alternans occurring in the second cardiac signal data, the processor can be configured to determine an onset heart rate of or a maximum negative heart rate for the second cardiac signal data.

The system can additionally include a display. The processor can be configured to generate display information based upon the results of the comparison and the display can be configured to render the display information generated by the processor.

In other implementations, some aspects include a computer-readable medium encoded with a computer program comprising instructions that, when executed, operate to cause a computer to perform operations. The operations include segmenting, into first cardiac signal data segments, cardiac signal data generated from measured heart beats of a subject, each first cardiac signal data segment including cardiac signal data of sequential heart beats. The operations also include determining, for each segment of the first cardiac signal data segments, characteristics of alternans occurring in the segment. The operations further include segmenting, into second cardiac signal data segments, cardiac signal data generated from measured heart beats of the subject after a change relating to an administration of a pharmacological agent, each second cardiac signal data segment including cardiac signal data of sequential heart beats. The operations additionally include determining, for each segment of the second cardiac signal data segments, characteristics of alternans occurring in the segment. Finally, the operations include comparing the characteristics of alternans occurring in the first cardiac signal data segments with the characteristics of alternans occurring in the second cardiac signal data segments.

This and other implementations can optionally include one or more of the following features, which also may optionally be in any combination. For example, the operations can include accessing the cardiac signal data from a non-volatile data storage previously interfacing with a device other than the device segmenting the cardiac signal data. Determining characteristics of alternans can include determining, for each segment of the first and second cardiac signal data segments, a presence of alternans in the segment, and comparing the characteristics can include determining a difference between the presence of alternans in the first cardiac signal data segments with the presence of alternans in the second cardiac signal data segments. Determining characteristics of alternans can include determining, for each segment of the first and second cardiac signal data segments, an onset heart rate of or maximum negative heart rate in the segment, and comparing the characteristics can include determining a difference between the onset heart rate of or maximum negative heart rate in the first cardiac signal data segments with the onset heart rate of or maximum negative heart rate in the second cardiac signal data segments.

Also, the operations can include determining, based upon the comparison, a difference in the subject's risk for ventricular tachyarrhythmias prior to the change relating to the administration of the pharmacological agent from the subject's risk for ventricular tachyarrhythmias after the change relating to the administration of the pharmacological agent. The cardiac signal data can be segmented such that the sequential order of the heart beats as measured by sensors is maintained within the first and second cardiac signal data segments. The cardiac signal data can be segmented such that the cardiac signal data in each cardiac signal data segment partially overlaps the cardiac signal data of another cardiac signal data segment. The operations can additionally include generating display information based upon the results of the comparison and rendering the generated display information.

In other implementations, some aspects include a method including receiving a cardiac signal data generated from measured heart beats of the subject after a change relating to an administration of a pharmacological agent, determining characteristics of alternans occurring in the received cardiac signal data, and comparing the characteristics of alternans occurring in the received cardiac signal data with the characteristics of alternans expected to be present prior to administration of the pharmacological agent.

The details of one or more implementations are set forth in the accompanying drawings and the description below. Other features will be apparent from the description and drawings, and from the claims

DETAILED DESCRIPTION

Pharmacological agents can increase a patient's risk of problems, such as sudden cardiac death or cardiac arrest from ventricular tachyarrhythmias (rapid heart rhythms). This potential of risk can be a significant burden to the development and use of pharmacological agents. One method to investigate the potential for a pharmacological agent to increase risks is measuring physiological characteristics of a patient before, during, and/or after the administration of an agent. For example, a patient's blood pressure can be measured before and after the patient is given a pharmacological agent to identify an increase in blood pressure, which generally indicates an increased risk of cardiovascular problems.

Figure 1:
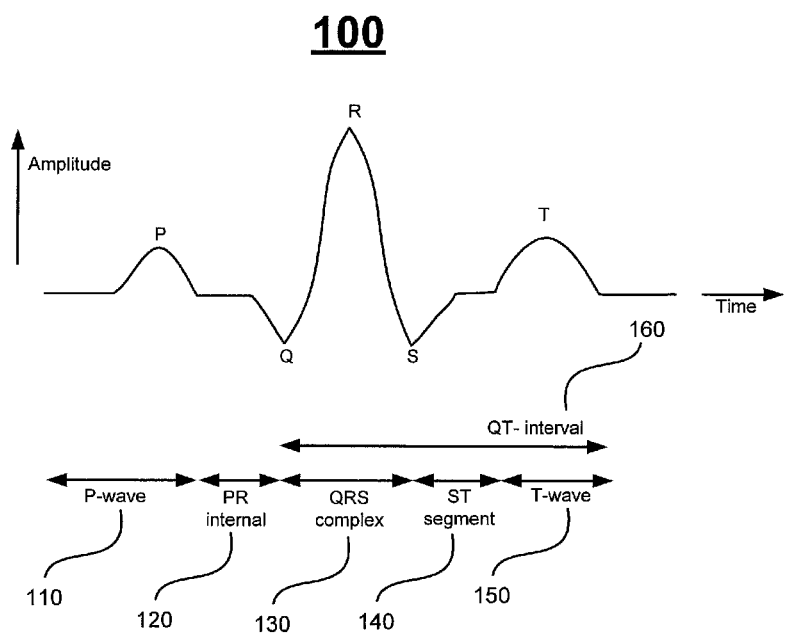
FIG. 1 is an example of an electrical waveform of a heart beat measured by an electrocardiography device to produce cardiac signal data.

To more specifically identify an increased risk of cardiac problems, characteristics of a heart beat can be measured. FIG. 1 is an example of a waveform 100 of a heart beat measured by an electrocardiography device to produce cardiac signal data. In particular, the waveform 100 is a measurement of a voltage between two electrodes placed on the body surface. The waveform 100 corresponds to a single heart beat. Various portions of the waveform 100 represent electrical activity in various structures of the heart. The P-wave 110 of the waveform 100 appears at initiation of the beat and corresponds to electrical activation of the atria of the heart. The PR interval 120 corresponds to the time between the end of the P-wave 110 and the onset of the QRS complex 130. There is normally no measurable electrical activity during the PR interval and this interval is often used to set the zero baseline of the recording. The QRS complex 130 corresponds to the electrical activation of the ventricles. The ST segment 140 represents the period between the end of the QRS complex and the onset of the T-wave 150 and corresponds to the portion of time during which the ventricles are activated (depolarized). In normal individuals, the ST segment tends to be relatively flat or slightly up-sloping and is approximately at the zero baseline. However, the ST segment can be shifted up or down or have a nonzero slope in patients with myocardial disease. The T-wave 150 reflects the electrical recovery of the ventricles. The QT interval 160 is the interval from the beginning of the QRS complex to the end of the T-wave and is used as a measure of the amount of time required for the ventricles to recover after initial activation.

One manner used to measure a pharmacological agent's tendency to predispose patients to ventricular tachyarrhythmias is the evaluation of prolongation of the QT interval 160. While the QT prolongation can be indicative of an increased risk for cardiac events, the QT interval 160 is, in some cases, prolonged from administration of pharmacological agents that do not actually predispose patients to ventricular tachyarrhythmias. As a result, some pharmacological agents which are deemed to prolong the QT interval 160 are never commercially developed even though they may not significantly predispose patients to ventricular tachyarrhythmias. Instead, other pharmacological agents that do not substantially prolong the QT interval 160 may be commercially developed and may nevertheless later be found to increase the risk of ventricular tachyarrhythmias. Moreover, a pharmacologic agent's tendency to increase risk of ventricular tachyarrhythmias may be highly patient specific and dependent on other factors, such as the presence of cardiac disease.

The presence of alternans can be used to indicate an increased risk of various medical problems which may accompany the administration of a pharmacological agent. Alternans is a beat-to-beat pattern of variation of an electrocardiographic complex (specifically, an every-other-beat pattern of beat-to-beat variation in the electrical activity of a heartbeat). For example, alternans has been linked to cardiac arrhythmia, cardiac arrest, sudden infant death syndrome, cardiac ischemia and the presence of coronary artery disease. The identification of an increase in presence or other characteristics of alternans after the administration of a pharmacological agent can be used to evaluate any increase in the patients' susceptibility to ventricular tachyarrhythmias, and to safely guide treatment of individual patients, particularly with pharmacological agents that are known or thought to increase susceptibility to ventricular tacharrhythmias for some patients.

Alternans can be an every-other-beat pattern of beat-to-beat variation in a portion of the waveform 100. The variation can be one shape or amplitude of the waveform portion. For example, T-wave alternans (also known as repolarization alternans) is alternans involving the T-wave. The presence of T-wave alternans can indicate electrical instability of the ventricles. T-wave alternans analysis of human or animal subjects can thus be used in the pharmacological development process to identify pharmacological agents less likely to predispose patients to ventricular tachyarrhythmias or in a patient's treatment plan to tailor the use of a pharmacological agent to the patient's physiological response to the agent. Alternans can also involve the QRS complex or the ST segment.

Clinically significant T-wave alternans may involve beat-to-beat variations in ECG waveform which are very small, involving as little as a few microvolts, and can be masked by other temporal patterns of beat-to-beat variability in the waveform 100. For example, skeletal muscle activity, electrode and cable motion, ambient electromagnetic activity, and device amplifiers all can introduce signal noise of a larger amplitude than that of the T-wave alternans. In the following description, T-wave alternans are generally referred to (rather than alternans of other portions of the waveform 100) for simplicity of understanding, though other alternans may be similarly measured and analyzed using the techniques described.

Alternans is generally measured as small voltage changes, such as a few microvolts, using an electrocardiogram (ECG) produced by an electrocardiography device operated by a doctor or technician. The ECG is a measurement of heart beats and can be produced in a controlled setting, such as a hospital or doctor's office, to obtain cardiac signal data at a desired heart rate while controlling for noise. This can involve techniques such as administering pharmacological agents for testing. The presence of alternans can increase with heart rate, so testing can also include placing a patient on a treadmill to intentionally elevate the heart rate and using an impedance measurement to factor out signal noise. Measuring alternans using an electrocardiography device for an extended period of time can be impractical, as the patient may be confined to a location of the electrocardiography device and the measurements can require the ongoing involvement of the technician or doctor.

An ambulatory electrocardiography device (AED) is a portable electrocardiography device configured to be worn on a patient's person. The patient wears the AED outside of the hospital or doctor's office without having their mobility significantly limited. An AED may also be an implanted device. The AED measures and stores cardiac signals for an extended period of time (e.g., 24 hours). Also, AEDs often do not include an impedance measurement as is sometimes used by electrocardiography devices. Consequently, the cardiac signal data produced by an AED can be of a wide range of heart rates and can have higher levels of noise. To compensate for these and/or other issues, the processing techniques used to analyze the AED's cardiac signal data to detect alternans can be different than those traditionally used to analyze the ECG of an electrocardiography device. Also, an AED can include input controls to enable a user, technician, or doctor to indicate the administration of a pharmacological agent and the AED can store or process measured data differently based upon the indicated administration.

Figure 2:
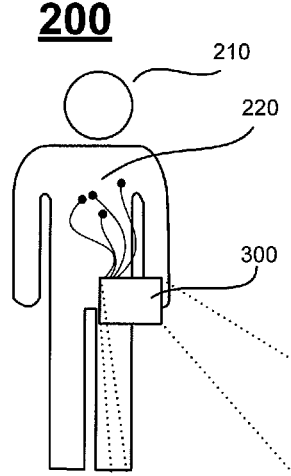
FIG. 2 is an illustration of a patient using an electrocardiography device to measure effects of a pharmacological agent.
Figure 3:
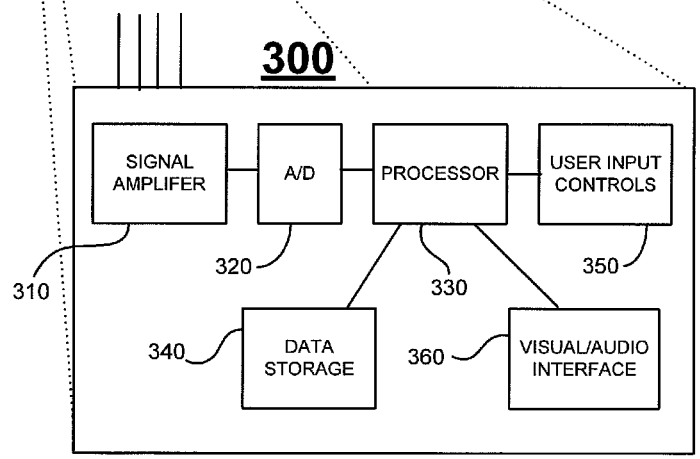
FIG. 3 is a schematic of a electrocardiography device to measure effects of a pharmacological agent.

FIG. 2 is an illustration 200 of a patient 210 using an electrocardiography device to measure effects of a pharmacological agent and FIG. 3. is an exemplary schematic of the electrocardiography device to measure effects of a pharmacological agent. For simplicity of understanding, the description below generally refers to the electrocardiography device as an AED 300. Nevertheless, the description of the AED 300 is also applicable to implementations using an electrocardiography device that is not ambulatory. An AED is generally used where mobility is desired (e.g., to enable prolonged analysis) and an electrocardiography device which is non-ambulatory can generally be otherwise used. With the AED 300, the cardiac signal data is processed to detect alternans in the cardiac activity of the patient 210 before, during, or after administration of a pharmacological agent. Also, the AED 300 enables a user to indicate the administration of the pharmacological agent to affect the storage or processing of the generated cardiac signal data.

Multiple electrodes 220 of the AED 300 are taped or otherwise attached to the chest of the patient 210 at particular locations of the patient's body to detect electrical activity from various sources. AEDs 300 generally use fewer electrodes 220 (e.g., three to eight) than electrocardiography devices (e.g., ten) to enhance device mobility. The AED 300 is generally worn at or around the patient's waist. This configuration enables the patient 210 to walk and otherwise be mobile while the AED 300 measures heart beats and records cardiac signals using the electrodes 220. As shown, the AED 300 includes a signal amplifier 310, an analog to digital converter 320, a processor 330, and data storage 340. The AED 300 can also include user input controls 350 and a visual or audio interface 360. These features of the AED 300 are exemplary, the AED can include different or additional features.

The signal amplifier 310 receives the cardiac signals measured from the electrodes 220 and amplifies them to produce amplified signal channels for processing. While an electrocardiography device typically can have 12 channels, AEDs generally have less, such as three or four channels. The signal amplifier 310 can be an instrumentation amplifier or another differential amplifier.

The amplified channels of the cardiac signals are digitized by the analog to digital converter 320 and then sent to the processor 330. Although not shown, one or more of the measured signals may be signals used to determine and adjust for noise rather than cardiac signals. For example, the AED 300 may include a signal line to measure respiration and a signal line to measure impedance. These techniques are described in more detail in U.S. Pat. No. 5,713,367, entitled "Measuring and accessing cardiac electrical stability," the contents of which are incorporated herein by reference.

In some implementations, the processor 330 generally is directed only to the storage of the digitized channels as cardiac signal data on the data storage 340 and communication of the cardiac signal data to another device. The user input controls 350 are configured to enable the user to indicate the administration of a pharmacological agent. For example, a user may be instructed to activate an input control (e.g., push a specific button on the AED 300) whenever the user administers a medication. The processor 330 can be configured to store the cardiac signal data based upon the activation of the user input control 350.

More specifically, cardiac signal data can be stored in a digital format including an agent administration "data header" indicating the time at which a user has last administered a pharmacological agent or change thereof. If the processor 330 segments cardiac signal data (described below), the processor 330 can store the agent administration data header along with each data segment. In one implementation, the cardiac signal data is stored without the agent administration data header until the user activates the user input control 350 to indicate the administration of an agent or change thereof. In another implementation, the cardiac signal data is always stored with the agent administration data header, but the value of the included agent administration data header changes based upon user activation of the user input control 350.

Therefore, other devices processing the stored cardiac signal data can read the agent administration data header and use the value/presence of the header to differentiate cardiac signal data generated prior to the administration of a pharmacological agent from cardiac signal data generated after the administration of a pharmacological agent. In some implementations, the user input controls 350 and the processor 330 are configured to enable the user to input more specific information, such as a type of medication, dosage of medication, or a present physical sensation. This more specific information can similarly be included in the agent administration data header or another data header stored with the cardiac signal data.

The data storage 340 can be a tangible computer-readable storage medium, such as, for example, a flash drive or a computer hard disk. The data storage 340 itself can be removable from the AED 300 to enable uploading of the cardiac signal data to a computer or other device. Also, the processor 330 can include a data communication port (e.g., a universal serial bus or Ethernet interface) to enable the AED 300 to interface with a computer to upload, display, or process the cardiac signal data. Additional computer hardware and functionality which can be included in the AED 300 is included in the description of FIG. 9.

In a more complex AED 300, the processor 330 may itself partially or completely process the cardiac signal data and may serve as an alternative to processing the cardiac signal data on a computer after uploading. Processing of the cardiac signal data is described in more detail in the description of the processes 400 and 500A-500B of FIGS. 4-5B. The processor 330 also can utilize the user input controls 350 and a visual or audio interface 360 to enable additional functionality to better enable the measurement of cardiac signals useful in detecting alternans. For example, T-wave alternans is more often detected at heart rates of between 100 and 120 BPM. The user input controls 350 and the visual or audio interface 360 can be used to communicate whether additional signal data is needed from such an accelerated heart rate. The patient 210 can use this information to determine whether it is necessary to spend time in a physically active state to facilitate the desired measurement of cardiac signals.

Also, the user input controls 350 and the visual or audio interface 360 can be used to communicate instructions or reminders relating to the administration or use of the pharmacological agent. For example, in one implementation, the visual or audio interface 360 will sound a reminder if a medication has not been indicated as administered by a point in time.

Figure 4:
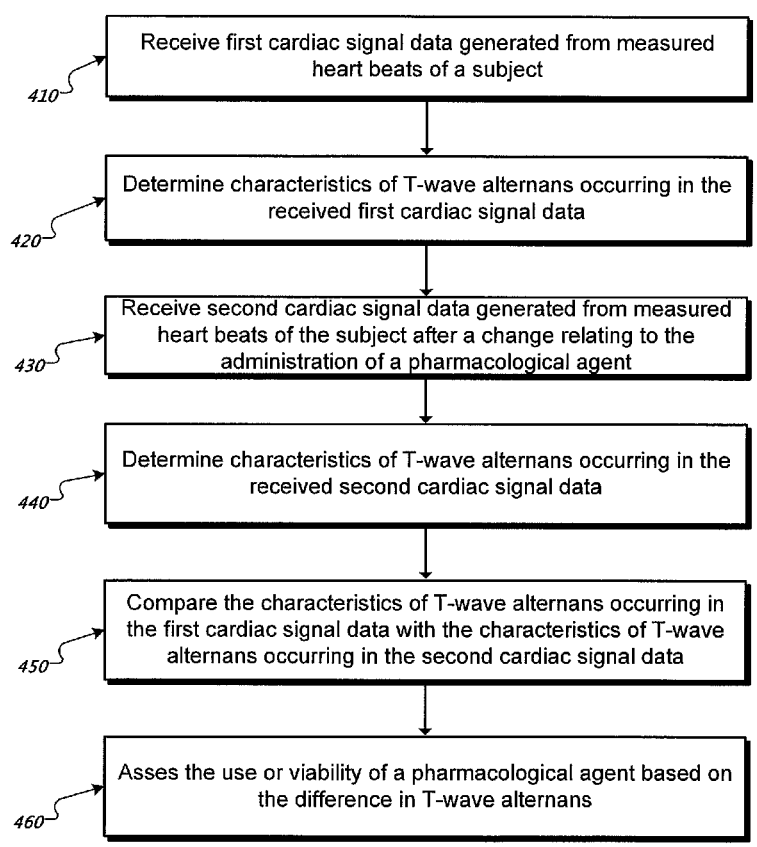
FIG. 4 is a block diagram of a process to evaluate alternans characteristics in conjunction with the use of a pharmacological agent.
Figure 5A:
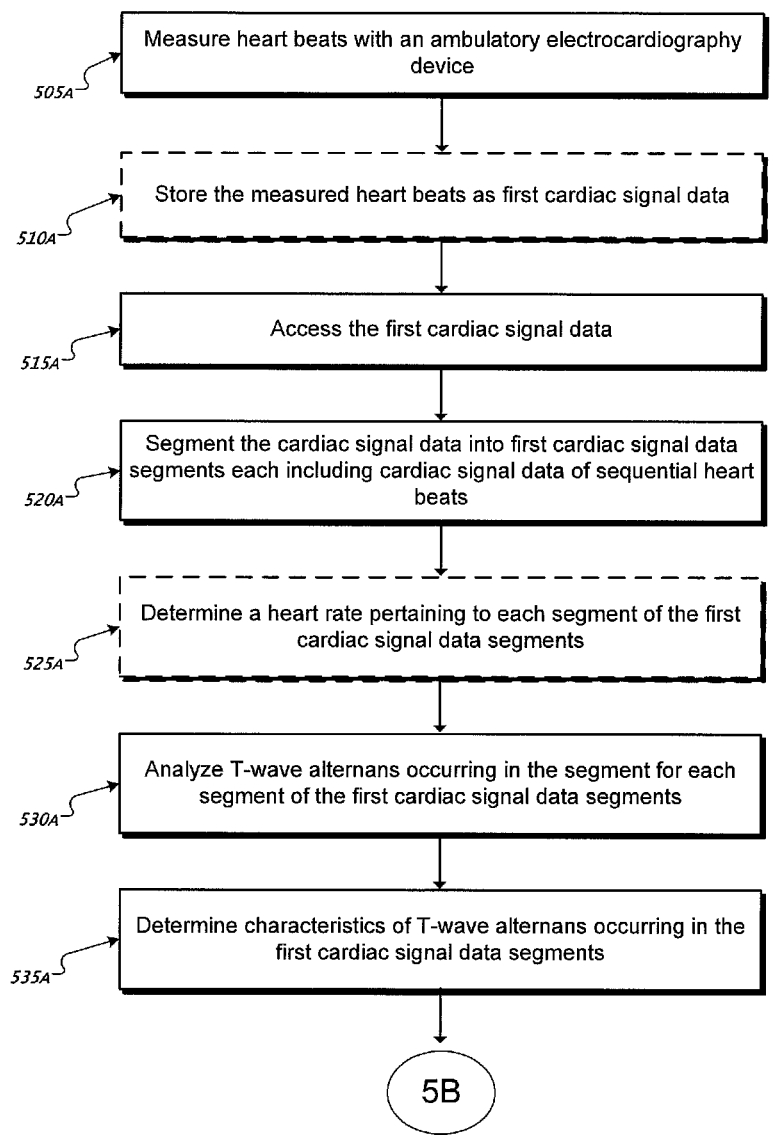
FIGS. 5A and 5B are block diagrams of a process to analyze segmented cardiac signal data to evaluate alternans characteristics in conjunction with the use of a pharmacological agent.
Figure 5B:
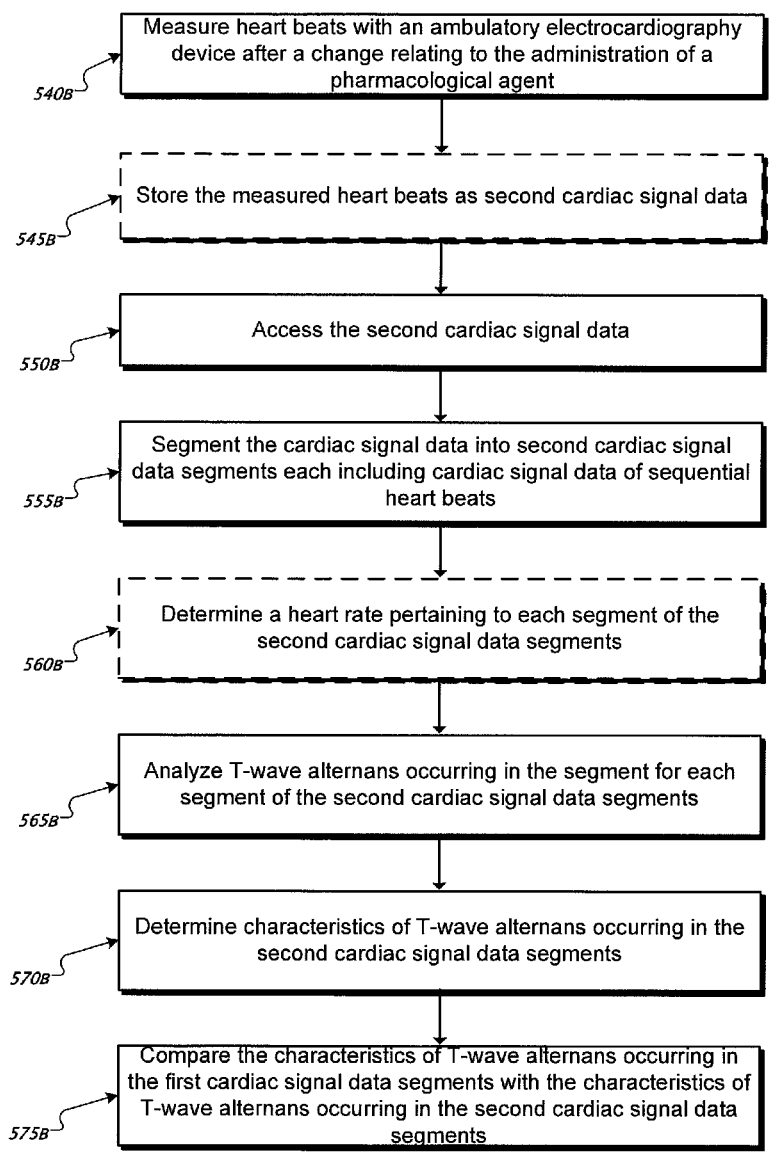

FIG. 4 is a block diagram of an example of a process 400 to evaluate alternans characteristics in conjunction with the use of a pharmacological agent and FIGS. 5A and 5B are block diagrams of a process 500A-500B to analyze segmented cardiac signal data to evaluate alternans characteristics in conjunction with the use of a pharmacological agent. The processes 400 and 500A-500B are described with respect to the features of FIGS. 2 and 3, though different electrocardiography devices and/or different features may be used. Also, the below description of the process 500A-500B refers to FIGS. 6-8, which are exemplary diagrams which can be representative of cardiac signal data analyzed during the process 500A-500B.

The processes 400 and 500A-500B of FIGS. 4-5B can be used in evaluation of a pharmacological agent's general safety, such as in a clinical trial. For example, the processes 400 and 500A-500B of FIGS. 4-5B can be carried out while monitoring a number of patients receiving the pharmacological agent. Also, the processes 400 and 500A-500B of FIGS. 4-5B can be used to determine whether, for a specific patient, a pharmacological agent is appropriate. In particular, a pharmacological agent may be available for use but known to have a propensity to increase risk of cardiac events for some patients. The processes 400 and 500A-500B of FIGS. 4-5B can be carried out with a particular patient to investigate that patient's physiological response to the pharmacological agent. If the results of the processes 400 and 500A-500B of FIGS. 4-5B indicate that risk is not increased (e.g., T-wave alternans did not increase in presence or otherwise worsen in characteristic), the patient may be put on a treatment plan including use of the pharmacological agent.

Specifically, FIG. 4 illustrates a process 400 to evaluate alternans characteristics in conjunction with the use of a pharmacological agent. Heart beats of a subject such as the patient 210 generate cardiac signals as voltages in the electrodes 220 which are measured by an electrocardiography device, such as the AED 300, to generate first cardiac signal data.

The first cardiac signal data generated from measured heart beats of the subject is received (410). In one implementation, the processor 330 or a module thereof can access the cardiac signal data as it is generated by the device. In another implementation, the processor 330 stores the measured heart beats as cardiac signal data in memory, and the stored data is later accessed by the AED 300 or another device. Whether the receipt of the cardiac signal data (410) is by the device generating the data or is by another device at a later time can depend on whether the device is a non-ambulatory electrocardiography device or an AED.

Characteristics of T-wave alternans occurring in the received first cardiac signal data are determined (420). In one implementation, the characteristics of T-wave alternans consist of the presence or absence of T-wave alternans in the first cardiac signal data, the amount of T-wave alternans in the first cardiac signal data, or the duration of T-wave alternans in the first cardiac signal data. In other implementations, the cardiac signal data is analyzed to determine additional characteristics. For example, a heart rate pertaining to portions of the first cardiac signal data can be determined, and, based on the determined heart rate, the characteristics can include an onset heart rate of T-wave alternans or a maximum heart rate below which T-wave alternans is not present ("maximum negative heart rate" with respect to T-wave alternans). Additional characteristics can include the magnitude of T-wave alternans, accompaniment of T-wave alternans with other waveform 100 phenomena, such as prolongation of the QT interval, ST segment changes indicative of ischemia or coronary artery disease, or other factors. The other waveform 100 phenomena, such as prolongation of the QT interval or ST segment changes indicative of ischemia or coronary artery disease, as discussed here are understood to be distinct from alternans in that these phenomena persist over multiple beats whereas alternans is a beat-to-beat pattern of variation.

The patient 210 is subjected to a change relating to the administration of a pharmacological agent. The change can be, for example, the initial administration of the pharmacological agent, an increase or decrease in dose of the pharmacological agent, or an accompaniment of the administration with an additional agent or physical activity. Heart beats of the patient 210 further generate cardiac signals as voltages in the electrodes 220 which are measured by the AED 300 to generate second cardiac signal data. The second cardiac signal data generated from measured heart beats of the subject after the change relating to the administration of a pharmacological agent is received (430). Characteristics of T-wave alternans occurring in the received second cardiac signal data are determined (440).

Thereafter, the characteristics of T-wave alternans occurring in the received first cardiac signal data are compared with the characteristics of T-wave alternans occurring in the received second cardiac signal data (450). The comparison can include a qualitative or quantitative examination of differences between the characteristics. In particular, a difference in T-wave alternans of the subject occurring prior to the change relating to the administration of a pharmacological agent from T-wave alternans of the subject occurring after the change relating to the administration of a pharmacological agent can be calculated. The difference can be one or more of the factors described above as characteristics, such as, for example, the difference in whether T-wave alternans is present or the difference in the amount (for example, the magnitude or power of the T-wave alternans) or duration of presence. Also, the difference in onset heart rate, maximum negative heart rate, or other factors can be calculated.

The results of these differences and/or the comparison can be used to then assess the use or viability of the pharmacological agent (460). In one implementation, patient independent use or viability of the pharmacological agent is assessed. For example, the pharmacological agent's general safety may be investigated as part of a clinical trial. In another implementation, patient specific use or viability of the pharmacological agent is assessed as part of the formation of the patient's treatment plan. For example, if the process 400 demonstrates evidence of increased susceptibility to ventricular tachyarrhythmias, the pharmacological agent may be either discontinued or the mode of its administration altered (e.g. change in dosage, change in dosing schedule, change in means of administration, or change in other aspects of patient medical management that may affect susceptibility to cardiac events, such as electrolyte management or administration of other agents which may interact with the pharmacological agent). Following a change in the mode of administration of the pharmacological agent, the process 400 may be repeated to assess the impact of the change on susceptibility to ventricular tachyarrhythmias. In this manner, a pharmacological agent which may predispose some patients to ventricular tachyarrhythmias may be more safely used.

In situations where the number of patients is large, the process 400 may be carried out without elements 410 and 420 (or similarly, without elements 505A-535A of the process 500A-500B). Specifically, the subject may be monitored only after the administration of the pharmacological agent. The alternans characteristics may be compared to a known expected alternans characteristic (e.g., what may be considered "normal" cardiac function), or, instead, to characteristics of a control group having never received the pharmacological agent. Also, the process 400 can be implemented in a different order. For example, element 420 can occur after element 430 (or similarly, elements 535A may occur after element any of elements 540B-565B of the process 500A-500B). Specifically, if the electrocardiography device used is the AED 300, the first and cardiac signal data may be generated and stored as cardiac signal data or segmented cardiac signal data (discussed below) on the AED 300. Thereafter, a separate computer can access, retrieve, and further process the first and second cardiac signal data.

FIGS. 5A and 5B illustrate a process 500A-500B to analyze segmented cardiac signal data to evaluate alternans characteristics in conjunction with the use of a pharmacological agent. The process 500A-500B can be particularly useful where data is recorded by an AED 300 for later processing by a separate device. Nevertheless, the process 500A-500B can also be carried out with data generated by an electrocardiography device as the data is generated. The description of the process 500A-500B can be applicable to the process 400 and vice versa.

Turning to the first portion of the process 500A, a subject, such as the patient 210, wears the AED 300 with the electrodes 220 taped to parts of his/her chest. The patient's heart beats generate cardiac signals as voltages in the electrodes 220. The heart beats are measured with the AED 300 (505A). Specifically, the AED 300 amplifies and digitizes the voltages from the electrodes 220 to enable digital signal processing by the processor 330 of the AED 300 to generate first cardiac signal data. The first cardiac signal data can be generated from measured heart beats of the patient 210 prior to a change pertaining to the pharmacological agent (e.g., initial administration of the agent).

In some implementations, the measured heart beats are stored as first cardiac signal data (510A) in the data storage 340. For example, many AEDs store the first cardiac signal data in transferable memory (e.g., a flash drive) to enable the data to be further processed elsewhere. The AED 300 may store the cardiac signal data along with one or more data headers indicating the nature of the data, such as indicating the data is before, during, or after administration of an agent or a change in the administration of an agent. In some implementations, the AED 300 stores the cardiac signal data without indicating information of the nature of the data until a user input control 350 is activated, and, thereafter, stores the cardiac signal data with a data header indicating the nature of the data.

The first cardiac signal data generated from heart beats measured with the AED 300 can be accessed by the AED 300 or a separate device (515A). By using the separate device in further processing, the AED 300 can be of minimal size and complexity. Nevertheless, a more advanced AED 300 with additional processing power and programming can implement the further processing discussed below without the use of a separate device.

Figure 6:
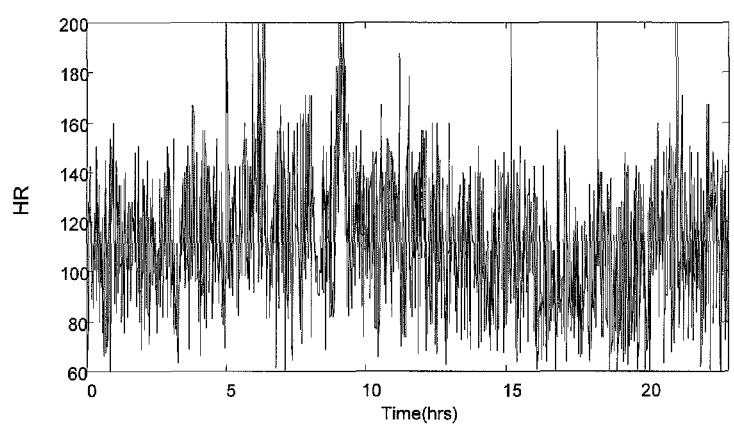
FIG. 6 is a diagram of a heart rate profile of cardiac signal data stored by an electrocardiography device.

FIG. 6 is a diagram 600 of an example of a heart rate profile of the first cardiac signal data stored by the AED 300. The diagram 600 shows the first cardiac signal data produced from the cardiac signals measured by the AED 300 during a 24 hour period. The first cardiac signal data is presented as heart rate as a function of time. The diagram 600 illustrates a challenge of using the first cardiac signal data produced by the AED 300 to detect alternans. As described above, alternans can be an every-other-beat pattern of variation in portions of the waveform of a measured cardiac signal. For example, T-wave alternans can be microvolt-level variations in the amplitude of the T-wave from one beat to the next, generally observed during heart rates of 100 to 120 BPM. Optimally, to detect T-wave alternans, the cardiac signal data is both at a heart rate of 100 to 120 BPM and is maintained at that level long enough to repeatedly analyze the beat-to-beat variation. However, the first cardiac signal data of the diagram 600 is not consistently at the desired heart rate and is not maintained at a given level. Although there are instances where the heart rate is between 100 and 120 BPM, these instances are scattered and not ideal for the detection of alternans.

The first cardiac signal data stored by the AED 300 is processed to convert the scattered cardiac data of the diagram 600 into more useful data, such as segments organized by associated heart rates. Simply sorting the first cardiac signal data by heart rate for each beat can foreclose the detection of variations between consecutive beats. Therefore, to preserve the beat-to-beat nature of the first cardiac signal data, the processing can involve segmenting data into groups of adjacent beats, determining features of the segments such as heart rate or whether a pharmacological agent has been administered, and sorting the segments by one or more features prior to processing to determine and compare T-wave alternans characteristics.

The cardiac signal data is segmented into first cardiac signal data segments (520A). Each segment of the first cardiac signal data segments includes data associated with multiple consecutive heartbeats. In one implementation, the segments are of 128 beats, but other segment sizes can be used. The segments can overlap beats so as to ensure the temporal relationship of beats is not lost. For example, the first 248 beats of cardiac signal data can be segmented into a first segment of beats 1 to 128 and a second segment of beats 120 to 248, leaving beats 120-128 included in both segments. Therefore, beat-to-beat variations in beats 120-128 can be compared to beats occurring just prior to beats 120-128 as well as to beats occurring just after beats 120-128.

Figure 7:
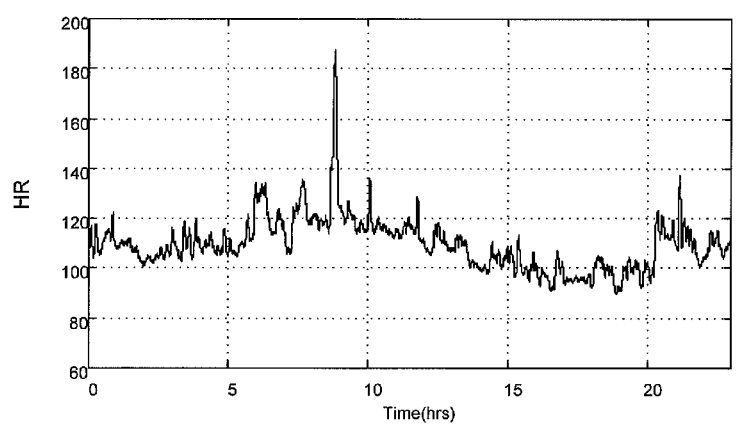
FIG. 7 is a diagram of a heart rate profile of segmented cardiac signal data generated from the cardiac signal data of FIG. 6.

In some implementations, a heart rate pertaining to each segment of the first cardiac signal data segment is determined (525A). In particular, a heart rate is separately calculated for each segment of the first cardiac signal data. The heart rate can be based on a simple averaging of the duration of each of the heart beats of a segment. FIG. 7 is a diagram 700 of an example of a heart rate profile of segmented first cardiac signal data generated from the first cardiac signal data of FIG. 6. The diagram 700 shows the segmented first cardiac signal data as heart rate as a function of time. Notably, the heart rate of the segmented first cardiac signal data in the diagram 700 fluctuates less dramatically than the heart rate of the first cardiac signal data of individual heart beats as shown in the diagram 600.

Figure 8:
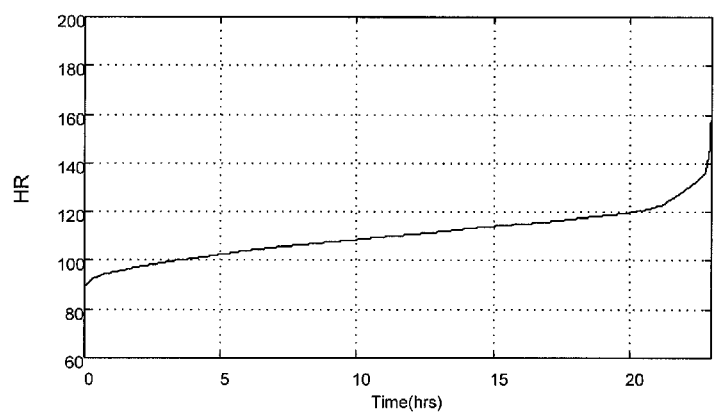
FIG. 8 is a diagram of sorted cardiac signal data generated from the segmented cardiac signal data of FIG. 7.

In some implementations, the first cardiac signal data segments are sorted into an order from the lowest determined heart rate to the highest determined heart rate. FIG. 8 is a diagram 800 of an example of sorted first cardiac signal data segments generated from the segmented first cardiac signal data of FIG. 7. The diagram 800 shows the distribution of heart rates for the segments after the segments have been ordered from the lowest determined heart rate to the highest determined heart rate. Although this exemplary distribution shows that the majority of the first cardiac signal data segments fall within the desired heart rate of 100 to 120 BPM, other distributions from other patients can have only a small fraction of the cardiac signal data segments within the desired heart rate.

T-wave alternans occurring in the segment are analyzed for each segment of the first cardiac signal data segments (or for each segment of the first cardiac signal data segments corresponding to suitable heart rates) (530A). In particular, each of the first cardiac signal data segments can be separately processed to detect alternans. Therefore, each of the cardiac signal data segments can have a unique determination of the presence of T-wave alternans.

Many implementations use spectral or analytic approaches to determine the presence of alternans in the first cardiac signal data segments. These approaches are described in detail in U.S. Pat. No. 7,197,358, entitled "Identifying Infants at Risk for Sudden Infant Death Syndrome," the contents of which are incorporated herein by reference. In the example above, where the first 248 beats of cardiac signal data are segmented into a first segment of beats 1 to 128 and a second segment of beats 120 to 248, the first segment is analyzed using the spectral or analytical approach to determine a first result, and the second segment is then analyzed using the spectral or analytical approach to determine a second result.

The analysis of the first cardiac signal data segments can also include processing dependent upon the determined heart rate or other characteristics of the first cardiac signal data segments. In some implementations, first cardiac signal data segments outside of a given range may be discarded or removed from further consideration. For example, first cardiac signal data segments with determined heart rates below 100 BPM or above 120 BPM may be excluded from further processing. In other implementations, processing is conducted differently based upon the determined heart rate. For example, first cardiac signal data segments with determined heart rates below 100 BPM may undergo a first type of further processing, whereas first cardiac signal data segments with determined heart rates above 100 BPM may undergo a second type of further processing.

Turning to the spectral approach, this approach uses measurements from time synchronized points of consecutive T-waves. For a segment of the first cardiac signal data segments, a time series is created by measuring, for each of the heart beats, the T-wave magnitude at a fixed location relating to the QRS component 120 of the waveform. This process is repeated to create a time series for each location in the T-wave of the heart beats in the segment. A frequency spectrum is then generated for each time series, and the spectra are averaged to form a composite T-wave alternans spectrum.

Since the T-waves are sampled once per beat for each time series, the spectral value at the Nyquist frequency, i.e. 0.5 cycles per beat, indicates the level of beat-to-beat alternation in the T-wave waveform. The alternans power is calculated from the composite T-wave alternans spectrum and statistically compared to the noise power to discriminate the beat-to-beat T-wave variation due to abnormal electrical activity of the heart from the random variation due to background noise. Alternans may be considered to be significant if the alternans exceed noise by a threshold amount, such as at least three times the standard deviation of the noise in a given noise reference band.

One example of how processing can be conducted differently based upon the determined heart rate is using a different threshold for determining whether alternans is significant for first cardiac signal data segments of different heart rate ranges. For example, alternans of first cardiac signal data segments with determined heart rates below 100 BPM may be considered significant if the alternans is at least double the standard deviation of the noise in the noise reference band, whereas alternans of first cardiac signal data segments with determined heart rates above 100 BPM may be considered significant if the alternans is at least triple the standard deviation of the noise in the noise reference band.

Turning to the analytic approach, this approach can be used to minimize the presence of noise or artifacts. First, a segment of the first cardiac signal data segments is low-pass filtered. In one implementation, the low pass filter is a $5^{th}$ order Butterworth filter with a zero phase configuration. The segment is transferred to the frequency domain using a fast Fourier transform (FFT). In the frequency domain, the portions of the frequency spectrum corresponding to negative frequencies are removed and all positive, non-zero components of the frequency spectrum are doubled to compensate. An inverse fast Fourier transform (IFFT) is then performed on the modified frequency spectrum to produce an analytical data segment in the time domain. Next, the analytical data segment is referenced to an analytical version of Wilson's central terminal (WCT), an ECG reference value. The analytical version of WCT is generated from the standard WCT using the procedures described in U.S. Pat. No. 7,197,358, title "Identifying infants at risk for sudden infant death syndrome" and U.S. Pat. No. 5,704,365, titled "Using Related Signals to Reduce ECG Noise," the contents of both are incorporated herein by reference. The analytical data segment is referenced to the analytical version of WCT by determining the difference between the two. The referenced analytical data segment then is processed.

If the data from the AED 300 includes signals used to determine and adjust for noise (e.g., signals related to respiration and impedance), the time series can be processed to reduce noise, such as that resulting from baseline wander. Techniques for processing the time series are described in more detail in U.S. Pat. No. 5,704,365, titled "Using Related Signals to Reduce ECG Noise," the contents of which are incorporated herein by reference.

Next, characteristics of T-wave alternans occurring in the first cardiac signal data segments is determined (535A). In some implementations, the characteristics of T-wave alternans includes the presence or absence of T-wave alternans in the first cardiac signal data segments, the amount of T-wave alternans in the first cardiac signal data segments, or the duration of T-wave alternans in the first cardiac signal data segments. For example, the determined characteristics can consist of a determination of the extent of the presence of T-wave alternans within the first cardiac signal data segments. Also, the determined characteristics can include the extent of the presence of alternans (e.g., the number of segments to which alternans occur, the average power of occurring alternans, or a function taking into account the amount of alternans presence and their power).

In other implementations, the first cardiac signal data segments are further analyzed to determine additional features as part of the determined characteristics. In particular, the occurrences of alternans in the first cardiac signal data segments can be compared to the context of the occurrences to determine further information. The context of the occurrence can include the heart rate pertaining to the cardiac data segment, the temporal position of a first cardiac signal data segment with alternans present relative to other first cardiac signal data segments, the consecutive duration of cardiac signal data segments with alternans, the time or heart rate of the first cardiac signal data segment with alternans present, or other considerations. For example, based on the determined heart rate of the cardiac signal data segments, the determined characteristics can include an onset heart rate of T-wave alternans or a maximum negative heart rate, for a particular segment or for all segments of the first cardiac signal data segments. Additionally, the determined characteristics can include the accompaniment of T-wave alternans with other waveform 100 phenomena, such as prolongation of the QT interval or ST segment changes which are indicative of ischemia or coronary artery disease.

Turning to the second portion of the process 500B, the patient 210 is subjected to a change pertaining to the administration of the pharmacological agent. For example, the patient 210 can be administered an initial dose of the agent, a changing dose of the agent, or a discontinuation of the agent. Also, the patient 210 can be subjected to a change in physical conditions with or without being given additional agent. For example, the patient 210 can be placed on a treadmill. The heart beats are then measured with the AED 300 after the change relating to the administration of a pharmacological agent (540B). In some implementations, the measured heart beats are stored as second cardiac signal data (545B) in the data storage 340. As stored, the second cardiac signal data may include a data header indicating the change pertaining to the administration of the pharmacological agent.

The second cardiac signal data generated from heart beats measured with the AED 300 can be accessed by the AED 300 or a separate device (550B). The cardiac signal data is segmented into second cardiac signal data segments (555B). Each segment of the second cardiac signal data segments includes data associated with multiple consecutive heartbeats. In some implementations, a heart rate pertaining to each segment of the second cardiac signal data segment is determined (560B). In particular, a heart rate is separately calculated for each segment of the second cardiac signal data segments. T-wave alternans occurring in the segment are analyzed for each segment of the second cardiac signal data segments (or for each segment of the second cardiac signal data segments corresponding to suitable heart rates) (565B). In particular, each of the second cardiac signal data segments can be separately processed to detect alternans. Therefore, each of the cardiac signal data segments can have a unique determination of the presence of T-wave alternans. Next, characteristics of T-wave alternans occurring in the second cardiac signal data segments are determined (570B).

The characteristics of T-wave alternans occurring in the first cardiac signal data segments are compared with the characteristics of T-wave alternans occurring in the second cardiac signal data segments (575B). The comparison can include a concurrent rendering of information of the characteristics of T-wave alternans occurring in the first and second cardiac signal data and/or can include a mathematical analysis of characteristics of T-wave alternans occurring in the first and second cardiac signal data. In particular, the comparison can include a calculation of the differences between one or more components of the characteristics. For example, the comparison can include a determination that alternans occurred in the second cardiac signal data segments twice as often as in the first cardiac signal data segments. Also, the comparison can include a determination regarding differences in other of the characteristics.

In some implementations, the comparison includes a calculation of a result which qualitatively or quantitatively indicates an increased risk. Specifically, a function taking into account multiple variables of the characteristics and weighing them according to importance or present value can be used to calculate a score. In one implementation, the score is a value between 0 and 10, with 0 indicating no known increased risk and 10 indicating a drastically increased risk. In some implementations, the score is determined by comparing the alternans onset heart rate and the distribution of heart rates with alternans. Further information about the analysis and classification of measured alternans can be found in U.S. Pat. No. 6,453,191 entitled "Automated Interpretation of T-wave Alternans Results," the contents of which are incorporated herein by reference.

Multiple functions may be used in the comparison which are specifically tailored to identify different risks. For example, in one implementation, the comparison includes calculating a first score using a first function tailored to determining an increased risk for one condition and a second score using a second function tailored to determining an increased risk for another condition. The comparison with or without calculated scores can be used to assess patient independent use or viability of the pharmacological agent or patient specific use or viability of the pharmacological agent. The process 500A-500B can be repeated to assess the impact of additional changes pertaining to administration of the pharmacological agent on susceptibility to ventricular tachyarrhythmias or other conditions.

Information of the processes 400 and 500A-500B can be made accessible by, for example, graphically displaying diagrams of data produced in the processes 400 and 500A-500B or the results of the comparison. The information of the processes 400 and 500A-500B can also be made accessible by storing diagrams of data produced in the processes 400 and 500A-500B or the results of the comparison in machine readable format.

As noted above, the processes 400 and 500A-500B can be carried out using the AED 300 to measure cardiac signals and store cardiac signal data and using a separate computer to conduct further processing. More advanced AEDs can be programmed to themselves carry out the processing of the processes 400 and 500A-500B. In some implementations, the AED 300 itself segments the data, analyzes occurrence of T-wave alternans, determines the characteristics, and/or compares the characteristics using the processor 330 of the AED 300 concurrent with the measuring of cardiac signal data. In these implementations, the AED 300 may store and access the cardiac signal data, generated cardiac signal data segments, determined characteristics, or any other information discussed above in and from volatile memory along with or instead of non-volatile memory to enable further processing to be carried out concurrently with measurement rather than after measurement. For example, in some implementations, the segmented first and second cardiac data is stored in the data storage 340 and the segmented first and second cardiac signal data is accessed by another device. Thereafter, the other device conducts the later elements of analyzing, determining characteristics, and comparing. In a further implementation, the results of the analysis of the segmented first and second cardiac data is stored in the data storage 340 and the results are accessed by another device and then compared.

The AED 300 can store all cardiac signal data segments along with and associated with the determined characteristics if any (e.g., heart rate, presence of alternans, or onset heart rate of alternans) in the data storage 340. Also, the AED 300 can store only cardiac signal data segments in the data storage 340 if a relevant characteristic is determined (e.g., only if the segment includes alternans or is within a desired heart rate). Also, live information of the analyzed alternans, the determined characteristics, or the comparison can be generated by the processor 330 and displayed to the patient 210 using the user input controls 350 and the visual or audio interface 360.

Figure 9:
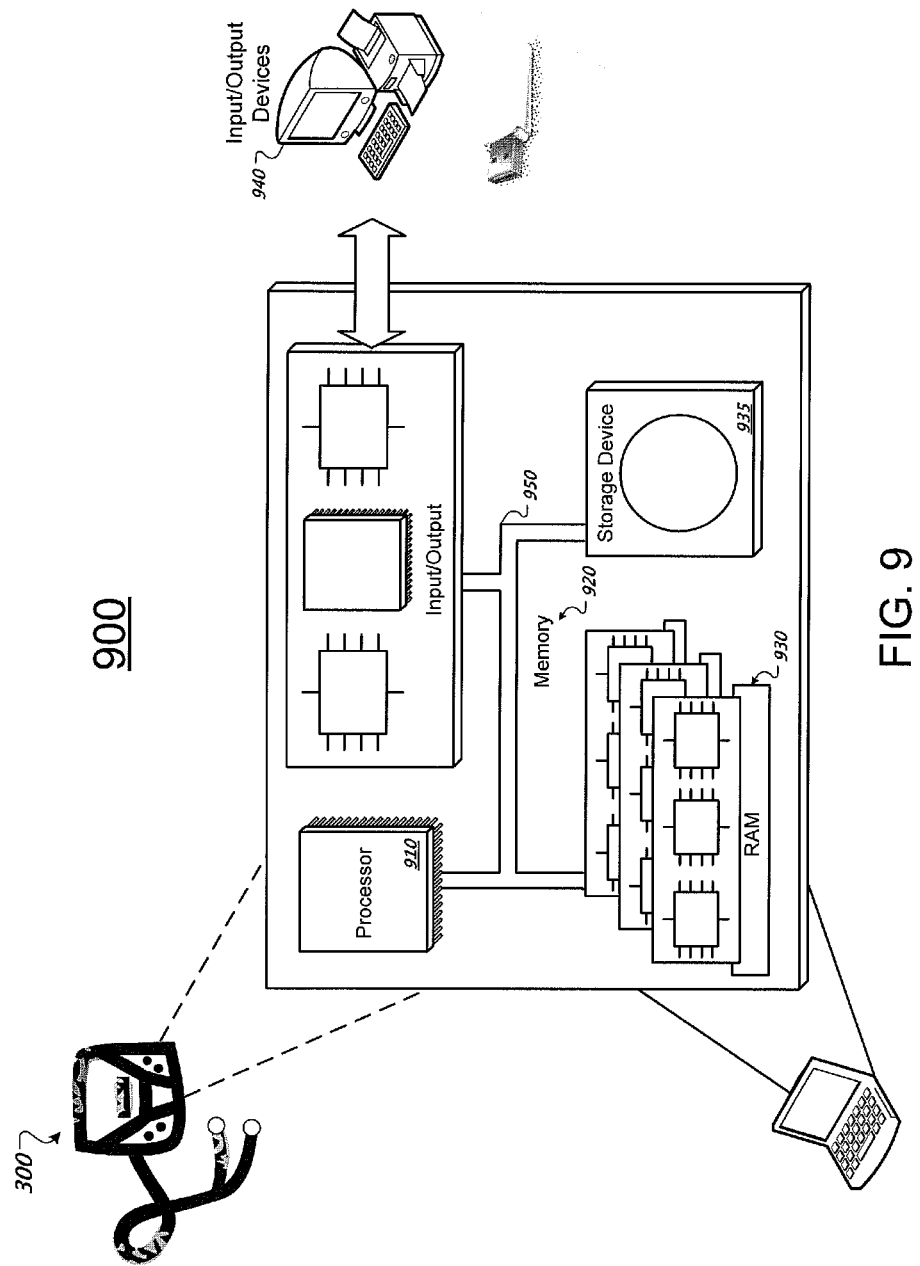
FIG. 9 is a schematic of a computer system configured to carry out the processes of FIGS. 4-5B.

FIG. 9 is a schematic of an example of a computer system 900 configured to carry out the processes 400 and 500A-500B of FIGS. 4-5B. While the computer system 900 is generally described as a separate device from the AED 300 of FIG. 3, the description of the computer system 900 can also apply to the hardware and functioning of the AED 300.

The computer system 900 includes a processor 910, memory 920, and an input/output device 940. The components 910, 920, and 940 are interconnected using a system bus 950. The processor 910 is capable of processing instructions for execution within the computer system 900. In one implementation, the processor 910 is a single-threaded processor. In another implementation, the processor 910 is a multi-threaded processor. The processor 910 is capable of processing instructions stored in the memory 920 to display graphical information for a user interface on the input/output device 940.

The memory 920 stores information within the computer system 900 and includes volatile memory 930 and non-volatile memory 935 and can be a computer-readable medium tangibly embodying instructions. The volatile memory 930 can include random access memory (RAM) and semiconductor memory devices (e.g., flip-flops or registers). The non-volatile memory 935 is capable of providing mass storage for the computer system 900. In various implementations, the non-volatile memory 935 can be a floppy disk device, a hard disk device, an optical disk device, or a tape device. Also, the non-volatile memory 935 can include, or be operatively coupled to communicate with, one or more mass storage devices for storing data files; such devices include magnetic disks, such as internal hard disks and removable disks, magneto-optical disks, optical disks, EPROM, EEPROM, flash memory devices, and CD-ROM, DVD-ROM, or Blu-ray™ disks.

The input/output device 940 provides input/output operations for the computer system 900. In one implementation, the input/output device 940 includes a keyboard and/or pointing device. In another implementation, the input/output device 940 includes a display unit for displaying graphical user interfaces. The input/output device 940 can include communications input/output operations. For example, the input/output device 940 can include a port for connection flash drives or other memory devices through a universal serial bus or other connection. Also, the input/output device 940 can include an Ethernet port for communication with other devices.

The features and processing described above can be implemented in a computer program product tangibly embodied in an information carrier, e.g., in a computer-readable medium encoded with a computer program product or in a machine-readable storage device for execution by a programmable processor; and features of the methods may be performed by a programmable processor executing a program of instructions to perform functions of the described implementations by operating on input data and generating output.

The described features and processing may be implemented advantageously in one or more computer programs that are executable on a programmable system including at least one programmable processor coupled to receive data and instructions from, and to transmit data and instructions to, a data storage system, at least one input device, and at least one output device. A computer program is a set of instructions that may be used, directly or indirectly, in a computer to perform a certain activity or bring about a certain result. A computer program may be written in any form of programming language, including compiled or interpreted languages, and it may be deployed in any form, including as a stand-alone program or as a module, component, subroutine, or other unit suitable for use in a computing environment.

Suitable processors for the execution of a program of instructions include, by way of example, both general and special purpose microprocessors, and the sole processor or one of multiple processors of any kind of computer. Generally, a processor will receive instructions and data from a read-only memory or a random access memory or both. The essential elements of a computer are a processor for executing instructions and one or more memories for storing instructions and data. The processor and the memory may be supplemented by, or incorporated in, ASICs (application-specific integrated circuits).

To provide for interaction with a user, the features may be implemented on a computer having a display device such as a CRT (cathode ray tube) or LCD (liquid crystal display) monitor for displaying information to the user and a keyboard and a pointing device such as a mouse or a trackball by which the user may provide input to the computer.

The components of the system may be connected by any form or medium of digital data communication such as a communication network. Examples of communication networks include, e.g., a LAN, a WAN, and the computers and networks forming the Internet.

A number of implementations have been described. Nevertheless, it will be understood that various modifications may be made without departing from the spirit and scope of the claims. For example, the flow diagrams depicted in the figures do not require the particular order shown, or sequential order, to achieve desirable results. In addition, other features may be provided, or features may be eliminated, from the described block diagrams, and other components may be added to, or removed from, the described devices. Accordingly, other implementations are within the scope of the following claims.

What is claimed is:

1. A method comprising:
receiving first cardiac signal data generated from measured heart beats of a subject;
determining, using at least one processor, characteristics of alternans occurring in the received first cardiac signal data;
receiving second cardiac signal data generated from measured heart beats of the subject after a change relating to an administration of a pharmacological agent to the subject;
determining characteristics of alternans occurring in the received second cardiac signal data; and
comparing the characteristics of alternans occurring in the received first cardiac signal data with the characteristics of alternans occurring in the received second cardiac signal data to assess an effect of the pharmacological agent on the subject.

2. The method of claim 1 wherein receiving first cardiac signal data includes accessing stored cardiac signal data from a non-volatile data storage.

3. The method of claim 1 wherein receiving first cardiac signal data includes accessing cardiac signal data from a volatile data storage which has not been stored in a non-volatile data storage.

4. The method of claim 1 wherein:
receiving first cardiac signal data includes receiving data generated from measured heart beats of a subject occurring prior to administration of the pharmacological agent; and
receiving second cardiac signal data includes receiving data generated from measured heart beats of a subject occurring after administration of the pharmacological agent.

5. The method of claim 1 wherein:
determining characteristics of alternans occurring in the received first cardiac signal data includes determining whether alternans is present in the received first cardiac signal data;
determining characteristics of alternans occurring in the received second cardiac signal data includes determining whether alternans is present in the received second cardiac signal data; and
comparing the characteristics includes determining a difference between the presence of alternans in the received first cardiac signal data with the presence of alternans in the received second cardiac signal data.

6. The method of claim 1 wherein:
determining characteristics of alternans occurring in the received first cardiac signal data includes determining a power or magnitude of alternans present in the received first cardiac signal data;
determining characteristics of alternans occurring in the received second cardiac signal data includes determining a power or magnitude of alternans present in the received second cardiac signal data; and
comparing the characteristics includes determining a difference between the power or magnitude of alternans in the received first cardiac signal data with the power or magnitude of alternans in the received second cardiac signal data.

7. The method of claim 1 wherein:
determining characteristics of alternans occurring in the received first cardiac signal data includes determining an onset heart rate of alternans present in the received first cardiac signal data;
determining characteristics of alternans occurring in the received second cardiac signal data includes determining an onset heart rate of alternans present in the received second cardiac signal data; and
comparing the characteristics includes determining a difference between the onset heart rate of alternans in the received first cardiac signal data with the onset heart rate of alternans in the received second cardiac signal data.

8. The method of claim 1 wherein:
determining characteristics of alternans occurring in the received first cardiac signal data includes determining a maximum negative heart rate in the received first cardiac signal data;
determining characteristics of alternans occurring in the received second cardiac signal data includes determining a maximum negative heart rate in the received second cardiac signal data; and
comparing the characteristics includes determining a difference between the maximum negative heart rate in the received first cardiac signal data with the maximum negative heart rate in the received second cardiac signal data.

9. The method of claim 1 wherein:
determining characteristics of alternans occurring in the received first cardiac signal data includes determining a presence or absence of alternans sustained for a period of time in the received first cardiac signal data;
determining characteristics of alternans occurring in the received second cardiac signal data includes determining a presence or absence of alternans sustained for a period of time in the received second cardiac signal data; and
comparing the characteristics includes determining the presence or absence of alternans sustained for a period of time in the received first cardiac signal data with the presence or absence of alternans sustained for a period of time in the received second cardiac signal data.

10. The method of claim 1 further comprising determining, based upon the comparison, a difference in the subject's risk for ventricular tachyarrhythmias prior to the change relating to the administration of the pharmacological agent from the subject's risk for ventricular tachyarrhythmias after the change relating to the administration of the pharmacological agent.

11. The method of claim 10 further comprising using the difference in the subject's risk for ventricular tachyarrhythmias to determine whether the pharmacological agent's use should be continued as treatment for an existing condition.

12. The method of claim 1 further comprising using the results of the comparison to assess the viability of the pharmacological agent for patients other than the subject.

13. The method claim 1 further comprising rendering results of the comparison.

14. The method of claim 1 wherein:
determining characteristics of the alternans occurring in the received first cardiac signal data includes determining characteristics of T-wave alternans occurring in the received first cardiac signal data;
determining characteristics of the alternans occurring in the received second cardiac signal data includes determining characteristics of T-wave alternans occurring in the received second cardiac signal data; and
comparing the characteristics of alternans occurring in the received first cardiac signal data with the characteristics of alternans occurring in the received second cardiac signal data includes comparing the characteristics of the T-wave alternans occurring in the received first cardiac signal data with the characteristics of the T-wave alternans occurring in the received second cardiac signal data.

15. The method of claim 1 wherein:
determining characteristics of the alternans occurring in the received first cardiac signal data includes determining characteristics of ST segment alternans occurring in the received first cardiac signal data;
determining characteristics of the alternans occurring in the received second cardiac signal data includes determining characteristics of ST segment alternans occurring in the received second cardiac signal data; and
comparing the characteristics of alternans occurring in the received first cardiac signal data with the characteristics of alternans occurring in the received second cardiac signal data includes comparing the characteristics of the ST segment alternans occurring in the received first cardiac signal data with the characteristics of the ST segment alternans occurring in the received second cardiac signal data.

16. The method of claim 1 wherein:
determining characteristics of the alternans occurring in the received first cardiac signal data includes determining characteristics of QRS complex alternans occurring in the received first cardiac signal data;
determining characteristics of the alternans occurring in the received second cardiac signal data includes determining characteristics of QRS complex alternans occurring in the received second cardiac signal data; and
comparing the characteristics of alternans occurring in the received first cardiac signal data with the characteristics of alternans occurring in the received second cardiac signal data includes comparing the characteristics of the QRS complex alternans occurring in the received first cardiac signal data with the characteristics of the QRS complex alternans occurring in the received second cardiac signal data.

17. The method of claim 1 further comprising:
determining QT prolongation or ST segment changes occurring in the received first cardiac signal data;
determining QT prolongation or ST segment changes occurring in the received second cardiac signal data; and comparing the QT prolongation or ST segment occurring in the received first cardiac signal data with the QT prolongation or ST segment occurring in the received second cardiac signal data.

18. The method of claim 1 further comprising assessing, based on the comparing of the characteristics of alternans occurring in the received first cardiac signal data with the characteristics of alternans occurring in the received second cardiac signal data, a risk of sudden cardiac death, sudden cardiac arrest, arrhythmias, or sudden infant death, or the presence of cardiac ischemia.

19. The method of claim 1 wherein:
receiving the first cardiac signal data generated from measured heart beats of the subject includes receiving, from an ambulatory electrocardiographic device, the first cardiac signal data generated from measured heart beats of the subject; and
receiving the second cardiac signal data generated from measured heart beats of the subject after the change relating to the administration of the pharmacological agent includes receiving, from the ambulatory electrocardiographic device, the second cardiac signal data generated from measured heart beats of the subject after the change relating to the administration of the pharmacological agent.

20. A non-transitory computer-readable memory encoded with a computer program comprising instructions that, when executed, operate to cause a computer to perform operations, the operations comprising:
segmenting, into first cardiac signal data segments, cardiac signal data generated from measured heart beats of a subject, each first cardiac signal data segment including cardiac signal data of sequential heart beats;
determining, for each segment of the first cardiac signal data segments, characteristics of alternans occurring in the segment;
segmenting, into second cardiac signal data segments, cardiac signal data generated from measured heart beats of the subject after a change relating to an administration of a pharmacological agent to the subject, each second cardiac signal data segment including cardiac signal data of sequential heart beats;
determining, for each segment of the second cardiac signal data segments, characteristics of alternans occurring in the segment; and
comparing the characteristics of alternans occurring in the first cardiac signal data segments with the characteristics of alternans occurring in the second cardiac signal data segments to assess an effect of the pharmacological agent on the subject.

21. The memory of claim 20 further comprising accessing the cardiac signal data from a non-volatile data storage previously interfacing with a device other than the device segmenting the cardiac signal data.

22. The memory of claim 20 wherein:
determining characteristics of alternans includes determining, for each segment of the first and second cardiac signal data segments, a presence of alternans in the segment; and
comparing the characteristics includes determining a difference between the presence of alternans in the first cardiac signal data segments with the presence of alternans in the second cardiac signal data segments.

23. The memory of claim 20 wherein:
determining characteristics of alternans includes determining, for each segment of the first and second cardiac signal data segments, an onset heart rate of or maximum negative heart rate in the segment; and
comparing the characteristics includes determining a difference between the onset heart rate of or maximum negative heart rate in the first cardiac signal data segments with the onset heart rate of or maximum negative heart rate in the second cardiac signal data segments.

24. The memory of claim 20 further comprising determining, based upon the comparison, a difference in the subject's risk for ventricular tachyarrhythmias prior to the change relating to the administration of the pharmacological agent from the subject's risk for ventricular tachyarrhythmias after the change relating to the administration of the pharmacological agent.

25. The memory of claim 20 wherein the cardiac signal data is segmented such that the sequential order of the heart beats as measured by sensors is maintained within the first and second cardiac signal data segments.

26. The memory of claim 20 wherein the cardiac signal data is segmented such that the cardiac signal data in each cardiac signal data segment partially overlaps the cardiac signal data of another cardiac signal data segment.

27. The memory of claim 20 further comprising:
generating display information based upon the results of the comparison; and
rendering the generated display information.

* * * * *